United States Patent
Guo et al.

(10) Patent No.: US 12,213,779 B2
(45) Date of Patent: Feb. 4, 2025

(54) SPORTS BRA SHOCK ABSORPTION EFFECT EVALUATION METHOD AND SYSTEM

(71) Applicants: Aimer Co., Ltd., Beijing (CN); Capital University of Physical Education and Sports, Beijing (CN)

(72) Inventors: Yunshan Guo, Beijing (CN); Ying Yan, Beijing (CN); Jingping Ren, Beijing (CN); Xinglong Zhou, Beijing (CN); Huijie Zhang, Beijing (CN)

(73) Assignees: AIMER CO., LTD, Beijing (CN); CAPITAL UNIVERSITY OF PHYSICAL EDUCATION AND SPORTS, Beijing (CN)

( * ) Notice: Subject to any disclaimer, the term of this patent is extended or adjusted under 35 U.S.C. 154(b) by 265 days.

(21) Appl. No.: 17/597,730

(22) PCT Filed: Feb. 7, 2021

(86) PCT No.: PCT/CN2021/075761
§ 371 (c)(1),
(2) Date: Jan. 20, 2022

(87) PCT Pub. No.: WO2021/160063
PCT Pub. Date: Aug. 19, 2021

(65) Prior Publication Data
US 2022/0265167 A1     Aug. 25, 2022

(30) Foreign Application Priority Data
Feb. 12, 2020   (CN) .......................... 202010088787.7

(51) Int. Cl.
*A61B 5/11*         (2006.01)
*A41C 3/00*         (2006.01)
(Continued)

(52) U.S. Cl.
CPC .......... *A61B 5/1114* (2013.01); *A41C 3/0057* (2013.01); *G01M 99/008* (2013.01); *G06F 17/11* (2013.01)

(58) Field of Classification Search
CPC ... A61B 5/1114; A61B 5/1121; A61B 5/1127; A41C 3/0057; A41C 5/00; G01M 99/008; G01M 99/00; G06F 17/11
See application file for complete search history.

(56) References Cited

U.S. PATENT DOCUMENTS 6,198,204 B1 *   3/2001   Pottenger ............... H10N 30/00
                                                 310/326
11,246,291 B1 *  2/2022   Landers ............... A01K 15/023
(Continued)

FOREIGN PATENT DOCUMENTS

CN      103445787 A    12/2013
CN      103838963 A     6/2014
(Continued)

OTHER PUBLICATIONS

Shang-xiao Li et al., "Influence of Sports Bra on Breast Kinematic Characteristics and the Gait Parameters Under Different Stride Frequencies", Chinese Master's Theses, Full-Text Database, Engineering Technology 1, Feb. 15, 2017, Abstract.*
(Continued)

*Primary Examiner* — Alexander Satanovsky
(74) *Attorney, Agent, or Firm* — TraskBritt

(57) ABSTRACT

A sports bra shock absorption effect evaluation method includes: allowing a subject to wear a sports bra for an experimental test, adhering a total of 43 infrared reflective mark points on the body, and completing preparation; allowing the subject naturally to stand on a treadmill, and acquiring static coordinate data; starting the treadmill, acquiring dynamic coordinate data for 5 minutes in sports when a speed in sports reaches 6-12 km/h, and immediately asking
(Continued)

a subjective perception of the subject after doing sports; converting the dynamic coordinate data into coordinate data in which a thoracic vertebra point is defined as an origin, and calculating a square root index S of displacement amplitude data in the left-right direction and the up-down direction; and numerically sorting the displacement amplitudes according to the square root index S, and corresponding to subjective perceptions one by one to obtain hierarchical definitions for an existing bra.

10 Claims, 3 Drawing Sheets

(51) Int. Cl.
  *G01M 99/00* (2011.01)
  *G06F 17/11* (2006.01)

(56) References Cited

U.S. PATENT DOCUMENTS

| | | | |
|---|---|---|---|
| 2012/0040588 | A1 | 2/2012 | Steele et al. |
| 2015/0151160 | A1* | 6/2015 | Balakrishnan ..... A63B 24/0021 700/91 |
| 2018/0333084 | A1* | 11/2018 | Wang ................ A61B 5/1127 |
| 2019/0075860 | A1 | 3/2019 | Ukoli |
| 2019/0174840 | A1* | 6/2019 | Paulson ............. A41C 3/0014 |

FOREIGN PATENT DOCUMENTS

| | | |
|---|---|---|
| CN | 108777161 A | 11/2018 |
| CN | 109579758 A | 4/2019 |
| CN | 111339480 A | 6/2020 |
| JP | 2000-096312 A | 4/2000 |
| WO | 2018/146015 A1 | 8/2018 |

OTHER PUBLICATIONS

Chinese First Office Action for Chinese Application No. 202010088787.7, dated Jan. 31, 2018, 8 pages with translation.

Great Britian Patent Examination Report No. 2 for Great Britian Application No. 2116721.8, dated Apr. 24, 2024, 4 pages.

Jie, et al., Analysis and evaluation of bra comfort based on breast displacement, China Academic Journal Electronic Publishing House, 1994-2023, 15 pgs.

Liang, et al., Numerical simulation of nonlinear material behaviour: Application to sports bra design, Materials and Design 183 (2019) 108177, 7 pgs.

McGhee, et al., Bra-breast forces generated in women with large breasts while standing and during treadmill running: Implications for sports bra design, Applied Ergonomics 44 (2013) 112-118, 7 pgs.

Monari, et al., The effect of different breast support conditions on multiplanar breast kinematics and kinetics during running, ESMAC 2012 Abstract/Gait & Posture 38 (2013) S1-S116, 1 pg.

International Search Report from International Application No. PCT/CN2021/075761, mailed Apr. 25, 2021, 7 pages.

International Written Opinion from International Application No. PCT/CN2021/075761, mailed Apr. 25, 2021, 8 pages.

Li, Shangxiao "Influence of Sports Bra on Breast Kinematic Characteristics and the Gait Parameters Under Different Stride Frequencies", Chinese Master's Theses Full-Text Database, Engineering Technology 1, (Feb. 15, 2017), pp. 5, 12-20, 37-43.

Chinese Search Report for Chinese Application No. 202010088787.7, dated Feb. 27, 2023, 3 pages.

Jie. Z. et al., "Analysis and Evaluation of Bra Comfort Based on Breast Displacement," Textile Industry, Issue 5, (2019), pp. 66-69, (English abstract only).

Li. C. et al., "unsynchronized frequency download Characteristics of breast movement caused by dynamic bra and the influence of gait parameters," Journal of Beijing Sport University, vol. 41, Issue 1, (2018).

* cited by examiner

SPORTS BRA SHOCK ABSORPTION EFFECT EVALUATION METHOD AND SYSTEM

CROSS-REFERENCE TO RELATED APPLICATIONS

This application is a national phase entry under 35 U.S.C. § 371 of International Patent Application PCT/CN2021/075761, filed Feb. 7, 2021, designating the United States of America and published as International Patent Publication WO 2021/160063 A1 on Aug. 19, 2021, which claims the benefit under Article 8 of the Patent Cooperation Treaty to Chinese Patent Application Ser. No. 202010088787.7, filed Feb. 12, 2020.

TECHNICAL FIELD

The present disclosure relates to the field of sports bras, and, in particular, to a method and a system for evaluating shock absorption effect of a sports bra.

BACKGROUND

With passage of time, more and more people begin to be concerned about their own health and do exercises. Sports equipment is also emerging in endlessly, with both intelligence and protection aspects. Effective protection against breasts is required due to particularity of women's physiological structures and a professional sports bra needs to be selected especially for women with full breasts or high-strength exercise. If an inappropriate sports bra is worn, movement of breasts not only is difficult to be controlled well and it may also cause breast pain. It can be seen that when purchasing a sports bra, most of the sports bras available on the market can be qualitatively and generally divided into three levels: low-strength sports bras, medium-strength sports bras and high-strength sports bras, but there is no method to quantitatively evaluate the shock absorption effect of the interaction between breasts and sports bras.

BRIEF SUMMARY

In view of the above problems, an evaluation method for shock absorption effect of a sports bra is provided, including:

step 1, making a preparation for a subject: allowing the subject to wear a sports bra for a test and adhering 43 infrared reflective mark points on the subject's body and completing the preparation;

step 2, acquiring static data: allowing the subject naturally to stand on a treadmill, and acquiring static coordinate data;

step 3, performing the test: starting the treadmill, acquiring dynamic coordinate data for 5 minutes during a sporting process when a speed of the treadmill reaches 6-12 km/h, and immediately asking subjective perceptions of the subject after doing sports;

step 4, converting coordinates: converting the dynamic coordinate data into coordinate data in which a thoracic vertebra point is defined as an origin, and calculating displacement amplitudes of subject's breast and a square root index $S=\sqrt{S^2_{left-right}+S^2_{up-down}}$ of the displacement amplitudes in a left-right direction and an up-down direction; and step 5: processing data: numerically sorting the displacement amplitudes according to the square root index S to obtain a grading range value, that is a grading definition for the sports bra.

According to an embodiment of the present disclosure, a system for evaluating shock absorption effect of a sports bra used for the method for evaluating shock absorption effect of a sports bra is provided, including: a data acquirer and a data processor communicated with each other. The data acquirer is configured to acquire static coordinate data and dynamic coordinate data of human's motion and the data processor is configured to perform coordinate conversion on data acquired by the data acquirer and calculate an average value of breast amplitudes during the human's motion.

According to an embodiment of the present disclosure, data points sampled by the data acquirer include 43 data points, including 29 points for a Helen Hayes model, 4 points for coordinate system conversion, and 10 points for recording breast movement.

According to an embodiment of the present disclosure, the dynamic coordinate data is acquired by the data acquirer in a dynamic state in which a speed of the treadmill is 10 km/h, and the acquisition time is 5 minutes.

According to an embodiment of the present application, the breast amplitudes calculation performed by the data processor takes the time between two consecutive heel strikes of a same foot in a gait cycle to calculate the square root index S of displacement amplitudes in the left-right direction and the up-down direction, respectively.

According to an embodiment of the present disclosure, the system for evaluating shock absorption effect of the sports bra further includes a feedback data storage module, the feedback data storage module is configured to acquire subjective perception data of the subject associated with two aspects of bra comfort and breast shaking amplitude. The feedback data storage module transmits the acquired data to the data processor, and the data processor is configured to sort the calculated amplitude data to obtain the bra grading range value.

According to an embodiment of the present disclosure, a coordinate conversion method used in the data processor includes:

step 1, establishing a global coordinate system: using X-axis as a frontal axis, and taking the right direction in left and right directions of human movement as a positive direction; using Y-axis as a sagittal axis, and taking the forward direction in forward and backward directions of human movement as a positive direction; using the Z-axis as a vertical axis, and taking an upward direction of vertical directions of human movement as a positive direction, thereby the global coordinate system is established;

step 2, establishing a breast coordinate system: using three points D1, D2 and D3 of a mid-sagittal plane of the human body to determine the breast coordinate system i, wherein D1 is a sternal angle point, D2 is a thoracic vertebra point and D3 is an eighth thoracic vertebra point; D1 and D2 have a same height, $\overrightarrow{D2D1}$ is Y axis, a normal vector $\vec{n}=\overrightarrow{D2D1}\times\overrightarrow{D2D3}$ of the plane determined by D1, D2 and D3 is X axis, $\overrightarrow{D2D1}\times\vec{n}$ is Z axis, X axis is in a left-right direction, taking the right direction as a positive direction; Y axis is in a forward-backward direction, taking the forward direction as a positive direction; Z axis is in a vertical direction, taking the upward direction as a positive direction and thus the breast coordinate system is established;

step 3, performing a conversion between the global coordinate system and breast coordinate system, wherein unit vectors of the global coordinate system are $\vec{e}_1$, $\vec{e}_2$, $\vec{e}_3$, unit vectors of the breast coordinate system are $\vec{f}_1$, $\vec{f}_2$, $\vec{f}_3$; for a point M, a vector $\overrightarrow{OM}$ is the sum of a vector $\overrightarrow{Oo}$ and a vector $\overrightarrow{oM}$, namely:

$$\overrightarrow{OM} = \overrightarrow{Oo} + \overrightarrow{oM} \quad (1)$$

the coordinate conversion is performed based on the equation (1); and step 4, calculating a coordinate value of a detection point under a motion state in the breast coordinate system, wherein at a time M, the detection point t has a coordinate $(x_{mt}, y_{mt}, z_{mt})$ in the global coordinate system and has a coordinate $(x'_{mt}, y'_{mt}, z'_{mt})$ in the breast coordinate system, and the coordinate of the original of the breast coordinate system in the global coordinate system is $(x_{ot}, y_{ot}, z_{ot})$, the equation (1) is represented by the unit vectors as follows:

$$x_{mt}\vec{e}_1 + y_{mt}\vec{e}_2 + z_{mt}\vec{e}_3 = (x_{ot}\vec{e}_1 + y_{ot}\vec{e}_2 + z_{ot}\vec{e}_3) + (x'_{mt}\vec{f}_1 + y'_{mt}\vec{f}_2 + z'_{mt}\vec{f}_3) \quad (2)$$

since $\vec{f}_1$, $\vec{f}_2$, $\vec{f}_3$ is converted from $\vec{e}_1$, $\vec{e}_2$, $\vec{e}_3$, namely, $$\begin{cases} \vec{f}_1 = a_{11}\vec{e}_1 + a_{21}\vec{e}_2 + a_{31}\vec{e}_3 \\ \vec{f}_2 = a_{12}\vec{e}_1 + a_{22}\vec{e}_2 + a_{32}\vec{e}_3 \\ \vec{f}_3 = a_{13}\vec{e}_1 + a_{23}\vec{e}_2 + a_{33}\vec{e}_3 \end{cases} \quad (3)$$

equation (4) is obtained from equations (2) and (3):

$$\begin{bmatrix} x'_{mt} \\ y'_{mt} \\ z'_{mt} \end{bmatrix} = \begin{vmatrix} a_{11} & a_{12} & a_{13} \\ a_{21} & a_{22} & a_{23} \\ a_{31} & a_{32} & a_{33} \end{vmatrix}^{-1} \begin{vmatrix} x_{mt} - x_{ot} \\ y_{mt} - y_{ot} \\ z_{mt} - z_{ot} \end{vmatrix} \quad (4)$$

calculating $$\begin{vmatrix} a_{11} & a_{12} & a_{13} \\ a_{21} & a_{22} & a_{23} \\ a_{31} & a_{32} & a_{33} \end{vmatrix}$$

based on the conversion relationship between the global coordinate system and the breast coordinate system and substituting calculated result into the equation (4) to obtain the coordinate $(x'_{mt}, y'_{mt}, z'_{mt})$ of the detection point in the breast coordinate system.

Beneficial Effects

Through the implementation of the evaluation method in the present disclosure, specific numbers are used to quantify and divide the strength of sports bra products, which may be more intuitive for consumers to buy, and the breast coordinate system is used to calculate the breast amplitude value, and calculation results are more in line with the actual state of human exercise and reflect the wearer's true feelings. In addition, the amplitude values are more accurate by using square root values in left-right and up-down directions.

DETAILED DESCRIPTION

Figure 1:
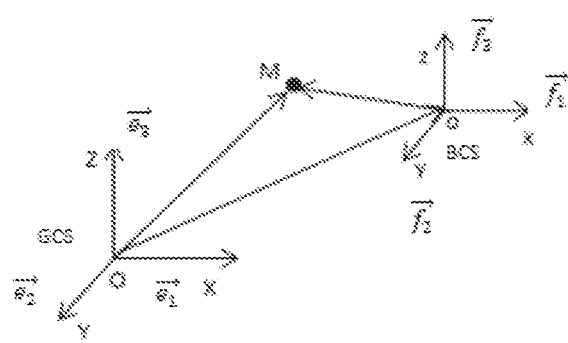
FIG. 1 is a schematic diagram of a global coordinate system GCS and a breast coordinate system BCS of the present application.
Figure 2:
FIG. 2 is a flow chart showing a method for evaluating shock absorption effect of a sports bra according to an embodiment of the present disclosure.

A method for evaluating shock absorption effect of a sports bra is provided, as shown in FIG. 2, including:

step 1, making a preparation for a subject: allowing the subject to wear a sports bra for a test and adhering 43 infrared reflective mark points on the subject's body and completing the preparation;

step 2, acquiring static data: allowing the subject naturally to stand on a treadmill, and acquiring static coordinate data;

step 3, performing the test: starting the treadmill, acquiring dynamic coordinate data for 5 minutes during a sporting process when a speed of the treadmill reaches 6-12 km/h, and immediately asking subjective perceptions of the subject after doing sports;

step 4, converting coordinates: converting the dynamic coordinate data into coordinate data in which a thoracic vertebra point is defined as an origin, and calculating displacement amplitudes of subject's breast and a square root index $S=\sqrt{S^2_{left-right} + S^2_{up-down}}$ of the displacement amplitudes in a left-right direction and an up-down direction;

step 5: processing data: numerically sorting the displacement amplitudes according to the square root index S to obtain a grading range value, that is a grading definition for the sports bra.

Figure 3:
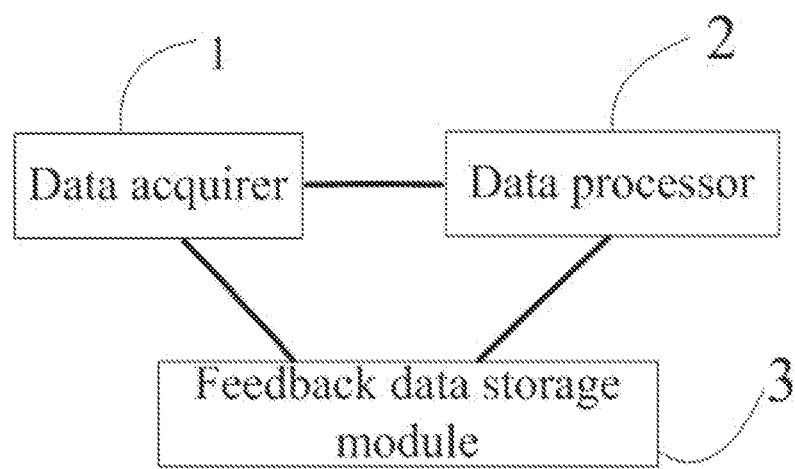
FIG. 3 is a schematic diagram showing a system for evaluating shock absorption effect of a sports bra according to an embodiment of the present disclosure.

In an embodiment of the present disclosure, a system for evaluating shock absorption effect of a sports bra used for the method for evaluating shock absorption effect of a sports bra is provided, as shown in FIG. 3, including: a data acquirer 1 and a data processor 2. The data acquirer 1 and the data processor 2 are communicated with each other to transmit data. The data acquirer 1 is configured to acquire static coordinate data and dynamic coordinate data of human's motion and the data processor 2 is configured to perform coordinate conversion on data acquired by the data acquirer (1) and calculate an average value of breast amplitudes during the human's motion.

Data points sampled by the data acquirer 1 include 43 data points, including 29 points for a Helen Hayes model (see Table 1), 4 points for coordinate system conversion (see Table 2), and 10 points for recording breast movement (see Table 3).

TABLE 1

Names and locations of the points in the Helen Hayes model

| Name of Mark Points | Position |
|---|---|
| Top Head | highest point of head when a subject is upright |
| Front Head | on sagittal plane in front of head |
| Rear Head | on sagittal plane on rear of head |
| L/R. Shoulder | acromion |

TABLE 1-continued

Names and locations of the points in the Helen Hayes model

| Name of Mark Points | Position |
|---|---|
| L/R. Elbow | external epicondyle of humerus |
| L/R. Wrist | midpoint of the connection between ulnar styloid and radius styloid |
| L/R. ASIS | anterior superior spine |
| L/R. Thigh | in front of thigh |
| L/R. knee | lateral femoral condyle |
| L/R. Knee Medial | medial femoral condyle |
| L/R. Calf | in front of calf |
| L/R. Ankle | lateral malleolus |
| L/R. Ankle Medial | medial malleolus |
| L/R. Toe | middle of second and third metatarsal head |
| L/R. Heel | calcaneal tuberosity |
| V. Sacral | midpoint of sacrum and fifth lumbar spinous processes |
| R. Offset | lower edge of right scapula |

TABLE 2

Points required for coordinate conversion

| Name | Position |
|---|---|
| vertebrae point | seventh cervical spinous process |
| sternal angle | midpoint of sternal angle |
| thoracic vertebral point (contour point of sternum angle) | approximately fourth to fifth thoracic vertebra spinous process |
| seventh to eighth thoracic vertebra | seventh to eighth thoracic vertebra spinous process |

TABLE 3

Points on the breast

| Name | Position |
|---|---|
| left and right breast points | nipples |
| upper point of left and right nipples | midpoint between a nipple and upper edge of a breast |
| lower point of left and right nipples | midpoint between a nipple and lower edge of breast |
| medial points of left and right nipples | midpoint between a nipple and medial edge of a breast |
| lateral points of left and right nipples | midpoint between a nipple and lateral edge of a breast |

The dynamic data are acquired by the data acquirer 1 under a dynamic state in which a speed is 10 km/h and the acquisition time is 5 minutes.

The breast amplitudes calculation performed by the data processor (2) takes the time between two consecutive heel strikes of a same foot in a gait cycle to calculate the square root index S of displacement amplitudes in the left-right direction and the up-down direction, respectively.

The system for evaluating shock absorption effect of the sports bra further includes a feedback data storage module 3, the feedback data storage module 3 is configured to acquire subjective perception data of the subject associated with two aspects of bra comfort and breast shaking amplitude. The feedback data storage module 3 transmits the acquired data to the data processor 2, and the data processor 2 is configured to sort the calculated amplitude data to obtain the bra grading range value. The bra comfort in the subjective perception can be divided into very uncomfortable, comfortable and very comfortable and the corresponding bra is divided into a low-strength bra, medium-strength bra and high-strength bra. The breast shaking amplitude is divided into small shaking, obvious shaking and severe shaking and the corresponding bra is divided into a high-strength bra, medium-strength bra and low-strength bra.

A coordinate conversion method used in the data processor 2 includes:

step 1, establishing a global coordinate system: using X-axis as a frontal axis, and taking the right direction in left and right directions of human movement as a positive direction; using Y-axis as a sagittal axis, and taking the forward direction in forward and backward directions of human movement as a positive direction; using the Z-axis as a vertical axis, and taking an upward direction of vertical directions of human movement as a positive direction, thereby the global coordinate system is established;

step 2, establishing a breast coordinate system: using three points D1, D2 and D3 of a mid-sagittal plane of the human body to determine the breast coordinate system i, wherein D1 is a sternal angle point, D2 is thoracic vertebral point (contour point of sternum angle) and D3 is an eighth thoracic vertebra point; D1 and D2 have the same height, $\overrightarrow{D2D1}$ is Y axis, a normal vector $\vec{n} = \overrightarrow{D2D1} \times \overrightarrow{D2D3}$ of the plane determined by D1, D2 and D3 is X axis, $\overrightarrow{D2D1} \times \vec{n}$ is Z axis, X axis is in left and right direction, the right direction is positive; Y axis is forward and backward direction, taking the forward direction as a positive direction; Z axis is in a vertical direction, taking the upward direction as a positive direction and thus the breast coordinate system is established;

step 3, performing a conversion between the global coordinate system and breast coordinate system, wherein unit vectors of the global coordinate system are $\vec{e_1}, \vec{e_2}, \vec{e_3}$; a unit vector of the breast coordinate system are $\vec{f_1}, \vec{f_2}, \vec{f_3}$; for any point M, a vector $\overrightarrow{OM}$ is the sum of a vector $\overrightarrow{Oo}$ and a vector $\overrightarrow{oM}$, namely:

$$\overrightarrow{OM} = \overrightarrow{Oo} + \overrightarrow{oM} \quad (1)$$

the coordinate conversion is performed based on the equation (1); and step 4, calculating a coordinate value of a detection point t under a motion state in the breast coordinate system, assuming that the coordinate of the detection point t at a time M in the global coordinate system is $x_{mt}, y_{mt}, z_{mt}$, and the coordinate of the detection point t at a time M in the breast coordinate system is $x'_{mt}, y'_{mt}, z'_{mt}$, and the coordinate of the original of the breast coordinate system in the global coordinate system is $x_{ot}, y_{ot}, z_{ot}$, the equation (1) may be represented by the unit vector:

$$x_{mt}\vec{e_1} + y_{mt}\vec{e_2} + z_{mt}\vec{e_3} = \left(x_{ot}\vec{e_1} + y_{ot}\vec{e_2} + z_{ot}\vec{e_3}\right) + \left(x'_{mt}\vec{f_1} + y'_{mt}\vec{f_2} + z'_{mt}\vec{f_3}\right) \quad (2)$$

since $\vec{f_1}, \vec{f_2}, \vec{f_3}$ is converted from $\vec{e_1}, \vec{e_2}, \vec{e_3}$, namely, $$\begin{cases} \vec{f_1} = a_{11}\vec{e_1} + a_{21}\vec{e_2} + a_{31}\vec{e_3} \\ \vec{f_2} = a_{12}\vec{e_1} + a_{22}\vec{e_2} + a_{32}\vec{e_3} \\ \vec{f_3} = a_{13}\vec{e_1} + a_{23}\vec{e_2} + a_{33}\vec{e_3} \end{cases} \quad (3)$$

Equation (4) can be obtained from equations (2) and (3):

$$\begin{bmatrix} x'_{mt} \\ y'_{mt} \\ z'_{mt} \end{bmatrix} = \begin{vmatrix} a_{11} & a_{12} & a_{13} \\ a_{21} & a_{22} & a_{23} \\ a_{31} & a_{32} & a_{33} \end{vmatrix}^{-1} \begin{vmatrix} x_{mt} - x_{ot} \\ y_{mt} - y_{ot} \\ z_{mt} - z_{ot} \end{vmatrix} \quad (4)$$

obtaining $$\begin{vmatrix} a_{11} & a_{12} & a_{13} \\ a_{21} & a_{22} & a_{23} \\ a_{31} & a_{32} & a_{33} \end{vmatrix}$$

by converting between the global coordinate system and the breast coordinate system and substituting it into the equation (4) to obtain the coordinate $x'_{mt}, y'_{mt}, z'_{mt}$ of any detection point in the breast coordinate system.

A verification method for the above evaluation method and evaluation system, includes the following steps:

step 1, processing data: corresponding subjective perception data collected in the above method and system to amplitude data measured by the subject one by one;

step 2, determining whether the subject's subjective perceptions correspond to the obtained grading range values; and step 3, the grading range values obtained by the evaluation method or evaluation system can be determined to be accurate when the strength grading corresponding to the subjective perceptions corresponds to the grading range obtained from the amplitude data, otherwise grading range values are inaccurate.

EMBODIMENT 1

The present disclosure is described below through specific embodiments.

step 1, recruiting female subjects, selecting several eligible subjects through professional measurement, with the test environment as 24-26° C.; the eligible subjects referring to subjects having the size of the bra to be measured;

step 2, allowing the subjects to wear uniform clothing including shorts and shoes and do warm-up exercises on the treadmill at a comfortable speed;

step 3, allowing the female subjects to wear sports bra used for the experimental test and adhering a total of 43 infrared reflective mark points having specific positions as shown in tables 1, 2 and 3 on their bodies, the data acquirer 1 may adopt an infrared motion capture system to capture and track the motion of reflective mark points, for example, Motion Analysis infrared motion capture system purchased available from American Motion Analysis Corporation. Eight lenses of the infrared motion capture system are evenly distributed over the test site and the height from the ground is above 2 meters to ensure that the reflective mark points on the subjects may be captured by the lens.

step 4, allowing the subject naturally to stand on a treadmill, finding a position where all the reflective mark points are not blocked, and acquiring static data for a few seconds for calibrating (a static calibration file is used for the calculation of coordinate conversion);

step 5, starting the treadmill, allowing the subjects to slowly accelerate to a speed of 10 km/h for running, acquiring dynamic coordinate data for 5 minutes in sports when a speed in sports reaches 6-12 km/h, and immediately asking subjective perceptions of the subject after doing sports;

subjective perceptions including bra comfort divided into very uncomfortable, comfortable and very comfortable and breast shaking amplitude divided into small shaking, obvious shaking and severe shaking;

step 6, identifying mark points from acquired data by a software that comes with Motion, exporting the corresponding file and converting coordinates of each point into coordinate positions in which a thoracic vertebra point is defined as an origin;

taking a duration from the left foot heel strike to the left foot heel strike again in a gait cycle, finding displacement amplitudes of points on the subject's breast in all directions during the gait cycle after wearing the sports bra and calculating a square root index $S=\sqrt{S^2_{left\text{-}right}+S^2_{up\text{-}down}}$ of the displacement amplitudes in a left-right direction and an up-down direction;

step 7, numerically sorting data of all experimental sports bras according to the square root index S, and corresponding to subjective perceptions one by one to obtain grading definitions for the sports bra.

After measuring the sports bra through the above method steps, several somatosensory theoretical data of B and C cup are obtained, and the comfort level is inferred from the corresponding grade, and then compared with the subjective questionnaire, which shows a consistent in the comparison results. The specific test results are as follows:

17 bras with B cup and 15 bras with C cup are tested. Test is performed on 6 to 10 women for each bra. All the data are sorted from small to large, the specific S value is shown in the following table:

|   | 1 | 2 | 3 | 4 | 5 | 6 | 7 | 8 | 9 |
|---|---|---|---|---|---|---|---|---|---|
| B | 19.7 | 20.1 | 21.0 | 23.1 | 23.5 | 23.6 | 24.3 | 25.8 | 29.4 |
| C | 24.4 | 25.1 | 25.3 | 26.1 | 27.0 | 28.6 | 29.6 | 29.8 | 31.3 |
|   | 10 | 11 | 12 | 13 | 14 | 15 | 16 | 17 |   |
| B | 32.0 | 32.2 | 33.6 | 35.4 | 36.0 | 37.4 | 38.4 | 38.6 |   |
| C | 31.6 | 34.0 | 35.0 | 36.0 | 38.5 | 40.0 |   |   |   |

According to the above sports bra test situation, the smaller the S value, the smaller the shaking amplitude, the higher the sports bra strength level, and the specific bra grading range value includes:

the boundaries between high-strength and medium-strength sports bras for B cup and C cup are at an S value of about 27.6 MM and an S value of about 29.7 MM, respectively, and the boundaries between medium-strength and low-strength sports bras for B cup and C cup are at an S value of about 35.7 MM and an S value of about 34.5 MM, respectively.

According to comparison between the subjects' subjective perceptions and grading ranges, it is concluded that taking B cup as an example, when the S value of the B cup is less than 27.6 MM, the subjects reported that the bra is very comfortable under exercise and the breast shaking amplitude is small during exercise, and the bra belongs to a high-strength sports bra; when the S value of the B cup is between 27.6 MM and 35.7 MM, the subjects reported that the bra is comfortable under exercise, and the breasts shake obviously during exercise, and the bra belongs to medium-strength sports bra; and when the S value of B cup is greater than 35.7 MM, the subjects reported that the bra is very uncomfortable under exercise, and the breasts shake severely during exercise, and the bra belongs to low-strength sports bras.

Obviously, the above-mentioned implementation of the present disclosure are merely examples to clearly illustrate the present disclosure, and are not intended to limit the implementations of the present disclosure. For those of ordinary skill in the art, other changes or modifications in different forms can be made on the basis of the above description. It is not possible to give an exhaustive list of all implementations here. Any obvious changes or changes derived from the technical solutions of the present disclosure are still within the scope of protection of the present invention as defined by the claims.

The invention claimed is:

1. A method for evaluating shock absorption effect of a sports bra, comprising:
    marking at least four data acquisition points on a subject, the at least four marked data acquisition points comprising a data acquisition point located proximate to each of a cervical vertebra, a thoracic vertebra, a sternal angle, and a breast of the subject, wherein the data acquisition point located proximate to a thoracic vertebra and the data acquisition point located proximate to a sternal angle are located at a same vertical height of the subject;
    acquiring static coordinate data from the at least four marked data acquisition points of the subject while the subject is wearing the sports bra and naturally standing on a treadmill, the static coordinate data acquired using a data acquirer configured to track the position of the at least four marked data acquisition points of the subject and communicate with a data processor configured to process data acquired by the data acquirer;
    starting the treadmill and acquiring dynamic coordinate data from the at least four marked data acquisition points of the subject within a preset period of time while the subject is wearing the sports bra and using the treadmill, the treadmill operating at a preset speed of 6 km/h or greater, the dynamic coordinate data acquired using the data acquirer;
    the static coordinate data being used for calculating coordinate conversion;
    converting the dynamic coordinate data into coordinate data in which a thoracic vertebra point is defined as an origin, and calculating displacement amplitudes of the subject's breast and a square root index $S = \sqrt{S^2_{left-right} + S^2_{up-down}}$ of the displacement amplitudes in a left-right direction and an up-down direction, the conversion and calculations performed by the data processor; and
    numerically sorting the displacement amplitudes based on the square root index S using the data processor, and obtaining a grading range value, that is a grading definition for the shock absorption effect of the sports bra worn by the subject.

2. The method of claim 1, further comprising:
    acquiring subjective perception data of the subject after the subject uses the treadmill at the preset speed for the preset period of time; and
    obtaining a second grading definition for the shock absorption effect of the sports bra worn by the subject based on the subjective perception data.

3. The method of claim 1, wherein the at least four marked data acquisition points comprises 43 marked data acquisition points.

4. A system for evaluating shock absorption effect of a sports bra used for the method for evaluating shock absorption effect of a sports bra according to claim 1, comprising:
    a data acquirer configured to acquire static coordinate data and dynamic coordinate data of the subject's motion; and
    a data processor in communication with the data acquirer, and configured to perform coordinate conversion on data acquired by the data acquirer and calculate an average value of breast amplitudes during the subject's motion.

5. The system of claim 4, wherein data points sampled by the data acquirer comprises 43 data points, including 29 points for a Helen Hayes model, 4 points for coordinate system conversion, and 10 points for recording breast movement.

6. The system of claim 4, wherein the dynamic coordinate data are acquired by the data acquirer under a dynamic state in which the preset speed of the treadmill is 10 km/h and the acquisition time is 5 minutes.

7. The system of claim 4, wherein the breast amplitudes calculation performed by the data processor takes the time between two consecutive heel strikes of a same foot in a gait cycle to calculate the square root index S of displacement amplitudes in the left-right direction and the up-down direction.

8. The system of claim 4, further comprising a feedback data storage module configured to acquire subjective perception data of the subject associated with two aspects of bra comfort and breast shaking amplitude, wherein the feedback data storage module transmits the acquired data to the data processor, and the data processor sorts the calculated amplitude data to obtain the bra grading range value.

9. The system of claim 4, wherein a coordinate conversion method used in the data processor comprises:
    step 1, establishing a global coordinate system having an origin O: using X-axis as a frontal axis, and taking the right direction in left and right directions of human movement as a positive direction; using Y-axis as a sagittal axis, and taking the forward direction in forward and backward directions of human movement as a positive direction; using the Z-axis as a vertical axis, and taking an upward direction of vertical directions of human movement as a positive direction, thereby the global coordinate system is established;
    step 2, establishing a breast coordinate system having an origin o: using three points D1, D2 and D3 of a mid-sagittal plane of the human body to determine the breast coordinate system i, wherein D1 is a sternal angle point, D2 is a thoracic vertebra point and D3 is an eighth thoracic vertebra point; D1 and D2 have a same height, $\overrightarrow{D2D1}$ is Y axis, a normal vector $\vec{n} =$ $\overrightarrow{D2D1} \times \overrightarrow{D2D3}$ of the plane determined by D1, D2 and D3 is X axis, $\overrightarrow{D2D1} \times \vec{n}$ is Z axis, X axis is in a left-right direction, taking the right direction as a positive direction; Y axis is in a forward-backward direction, taking the forward direction as a positive direction; Z axis is in a vertical direction, taking the upward direction as a positive direction and thus the breast coordinate system is established;

step 3, performing a conversion between the global coordinate system and breast coordinate system, wherein unit vectors of the global coordinate system are $\vec{e}_1, \vec{e}_2, \vec{e}_3$; unit vectors of the breast coordinate system are $\vec{f}_1, \vec{f}_2, \vec{f}_3$; for a point M, a vector $\overrightarrow{OM}$ is the sum of a vector $\overrightarrow{Oo}$ and a vector $\overrightarrow{oM}$, namely:

$$\overrightarrow{OM} = \overrightarrow{Oo} + \overrightarrow{oM} \quad (1)$$

the coordinate conversion is performed based on the equation (1); and step 4, calculating a coordinate value of a detection point under a motion state in the breast coordinate system, wherein at a time M, the detection point t has a coordinate $(x_{mt}, y_{mt}, z_{mt})$ in the global coordinate system and has a coordinate $(x'_{mt}, y'_{mt}, z'_{mt})$ in the breast coordinate system, and the coordinate of the original of the breast coordinate system in the global coordinate system is $(x_{ot}, y_{ot}, z_{ot})$, the equation (1) is represented by the unit vectors as follows:

$$x_{mt}\vec{e}_1 + y_{mt}\vec{e}_2 + z_{mt}\vec{e}_3 = (x_{ot}\vec{e}_1 + y_{ot}\vec{e}_2 + z_{ot}\vec{e}_3) + (x'_{mt}\vec{f}_1 + y'_{mt}\vec{f}_2 + z'_{mt}\vec{f}_3) \quad (2)$$

since $\vec{f}_1, \vec{f}_2, \vec{f}_3$ is converted from $\vec{e}_1, \vec{e}_2, \vec{e}_3$, namely, $$\begin{cases} \vec{f}_1 = a_{11}\vec{e}_1 + a_{21}\vec{e}_2 + a_{31}\vec{e}_3 \\ \vec{f}_2 = a_{12}\vec{e}_1 + a_{22}\vec{e}_2 + a_{32}\vec{e}_3 \\ \vec{f}_3 = a_{13}\vec{e}_1 + a_{23}\vec{e}_2 + a_{33}\vec{e}_3 \end{cases} \quad (3)$$

equation (4) is obtained from equations (2) and (3):

$$\begin{bmatrix} x'_{mt} \\ y'_{mt} \\ z'_{mt} \end{bmatrix} = \begin{vmatrix} a_{11} & a_{12} & a_{13} \\ a_{21} & a_{22} & a_{23} \\ a_{31} & a_{32} & a_{33} \end{vmatrix}^{-1} \begin{vmatrix} x_{mt} - x_{ot} \\ y_{mt} - y_{ot} \\ z_{mt} - z_{ot} \end{vmatrix} \quad (4)$$

calculating $$\begin{vmatrix} a_{11} & a_{12} & a_{13} \\ a_{21} & a_{22} & a_{23} \\ a_{31} & a_{32} & a_{33} \end{vmatrix}$$

based on the conversion relationship between the global coordinate system and the breast coordinate system and substituting the calculated result into the equation (4) to obtain the coordinate $(x'_{mt}, y'_{mt}, z'_{mt})$ of the detection point in the breast coordinate system.

10. The system of claim 4, wherein the treadmill is set to the preset speed of 6 to 12 km/h and the preset period of time is 5 min.

\* \* \* \* \*